(12) United States Patent
Pecharsky et al.

(10) Patent No.: US 6,730,812 B2
(45) Date of Patent: May 4, 2004

(54) SOLVENT-FREE MECHANOCHEMICAL PREPARATION OF PHOSPHONIUM SALTS, PHOSPHORUS YLIDES, AND OLEFINS

(75) Inventors: Vitalij K. Pecharsky, Ames, IA (US); Viktor P. Balema, Ames, IA (US); Jerzy W. Wiench, Ames, IA (US); Marek Pruski, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 10/358,552

(22) Filed: Feb. 5, 2003

(65) Prior Publication Data

US 2003/0176740 A1 Sep. 18, 2003

Related U.S. Application Data

(60) Provisional application No. 60/354,825, filed on Feb. 6, 2002.

(51) Int. Cl.$^7$ ............................. C07F 9/54; C07F 9/535
(52) U.S. Cl. .................................. 568/9; 568/8
(58) Field of Search ........................ 568/9, 8; 560/8, 560/55

(56) References Cited

U.S. PATENT DOCUMENTS

| | | | | |
|---|---|---|---|---|
| 2,905,717 A | * | 9/1959 | Sarnecki et al. | 568/11 |
| 3,524,886 A | * | 8/1970 | Fried | 568/9 |
| 3,538,013 A | | 11/1970 | Graff | |
| 4,122,123 A | * | 10/1978 | Hestermann et al. | 568/9 |
| 4,182,731 A | * | 1/1980 | Schulz et al. | 568/9 |

OTHER PUBLICATIONS

Journal of the American Chemical Society Communictaions by Balema et al 124 pp 6244–5 web published May 10, 2002.*
CA:96:85024 abs of Synthesis by Bestmann (12) pp 998–9 1981.*

* cited by examiner

*Primary Examiner*—Jean F. Vollano
(74) *Attorney, Agent, or Firm*—Leydig, Voit & Mayer, Ltd.

(57) ABSTRACT

The present invention provides a method of preparing a phosphonium salt of the formula $[R^1R^2R^3P-CR^4R^5R^6]X$, comprising ball-milling a phosphine of the formula $R^1R^2R^3P$ with a compound of the formula $XCR^4R^5R^6$; a method of preparing a phosphorus ylide of the formula $R^1R^2R^3P=CR^4R^5$, comprising ball-milling a phosphonium salt of the formula $[R^1R^2R^3P-HCR^4R^5]X$ in the presence of a base; and a method of preparing an olefin of the formula $R^4R^5C=CR^7H$ or $R^4R^5C=CR^7R^8$, comprising ball-milling a phosphorus ylide of the formula $R^1R^2R^3P=CR^4R^5$ with a compound of the formula $R^7C(O)H$ or $R^7C(O)R^8$. The inventive method produces phosphonium salts and phosphorus ylides by mechanical processing solid reagents under solvent-free conditions. The advantages of the present invention over conventional solution methods, include: (1) extremely high selectivity; (2) high yields; (3) low processing temperatures; (4) simple and scalable reactions using commercially available equipment; and (5) the complete elimination of solvents from the reaction.

12 Claims, 5 Drawing Sheets

SOLVENT-FREE MECHANOCHEMICAL PREPARATION OF PHOSPHONIUM SALTS, PHOSPHORUS YLIDES, AND OLEFINS

CROSS-REFERENCE TO RELATED PATENT APPLICATIONS

This patent application claims the benefit of U.S. patent application Ser. No. 60/354,825, which was filed on Feb. 6, 2002.

STATEMENT REGARDING FEDERALLY SPONSORED RESEARCH AND DEVELOPMENT

This invention was made in part with Government support under Contract Number W-7405-ENG-82 awarded by the Department of Energy (DOE). The Government may have certain rights in this invention.

FIELD OF THE INVENTION

This invention pertains to the solvent-free mechanochemical preparations of phosphonium salts and phosphorus ylides, and to utilizing such phosphorus ylides in carrying out the solvent-free synthesis of desired unsaturated organic compounds employing the Wittig-Horner reaction (also known as the Wittig reaction).

BACKGROUND OF THE INVENTION

Phosphonium salts are used as agricultural chemicals, phase transfer catalysts, physiologically active compounds, corrosion inhibitors, flame retardants, anti-static and softening agents (see, e.g., WO 99/28287; JP 2000-265085; EP 139260; U.S. Pat. Nos. 4,246,031; and 4,943,380). However, the current major application of phosphonium salts is considered to be their transformation into phosphorus ylides, which phosphorus ylides further participate in the Wittig-Horner reaction leading to diverse unsaturated organic compounds (W. A. Johnson, *Ylides and imines of phosphorus*. John Wiley & Sons, Inc. New York, 1993).

Typically, phosphonium salts are synthesized in solution by a broad variety of methods, which include reactions of phosphines with alcohols or oxiranes, with aromatic organic halides in the presence of metal salts, or with diazo compounds (P. Beck in *Organic Phosphorus Compounds vol. 2*, Eds.: G. M. Kosolapoff, L. Maier, John Wiley & Sons, Inc. New York, p. 189, 1972; DE 19914193; K. Sasse in *Methoden der Organischen Chemie (Houben-Weil)*, Bd XII/1, Ed.: E. Müller, Georg Thieme Verlag, Stuttgart, p. 79, 1963; K. Jödden in *Methoden der Organischen Chemie (Houben-Weil)*, Bd E1, Ed.: M. Regitz, Georg Thieme Verlag, Stuttgart, New York, p. 491, 1982). A conventional method of preparing alkyl-substituted phosphonium salts is the reaction of ternary phosphines with alkyl halides in appropriate organic solvents. Alternatively, liquid organic halides can be used as the reaction media. Although successful in many instances, the preparation of phosphonium salts from phosphines and alkyl halides using these methods can be complicated by side reactions, thus lowering the overall yield of the desired compounds. In particular, reactions of ternary phosphines with α-bromoketones are unreliable because alkylation of phosphines is accompanied by the formation of O-phosphorylated products and by the dehydrobromination of the starting bromoketones (W. A. Johnson, *Ylides and imines of phosphorus*. John Wiley & Sons, Inc. New York, 1993; Borowitz et al., *J. Org. Chem.* 34, 1595 (1969)).

In the presence of a base, phosphonium salts can form phosphorus ylides. Phosphorus ylides find use in the synthesis of vitamins, terpenoids, steroids, hormones, prostaglandins, amino acids, nucleotides, physiologically active compounds, and transition metal complexes, and in polymerization processes. However, as previously noted, it is believed that the major use of phosphorus ylides is their reaction with diverse organic carbonyl derivatives in the Wittig-Homer reaction, which allows for the preparation of various unsaturated organic substances. Conventionally and exclusively, the generation of phosphorus ylides is performed in a solution using a wide variety of solvents (see, e.g., W. A. Johnson, *Ylides and imines of phosphorus*. John Wiley & Sons, Inc. New York, 1993; WO 99/28287; Hudson in *The Chemistry of Organophosphorus Compounds vol. 1*, Ed.: F. R. Hartley, John Wiley & Sons, Ltd. New York, p. 386, 1990; *The Chemistry of Organophosphorus Compounds, vol. 3: Phosphonium Salts, Ylides and Phosphoranes*. Ed.: F. R. Hartley, John Wiley & Sons, Ltd. New York, 1994).

Additionally, the bases used in the preparation of such phosphorus ylides should possess an appropriate strength, as is known. Examples of suitable bases include alkali metal carbonates, alkali metal hydroxides, alkali metal alkoxides, methyl, butyl or phenyllithium. As with the preparation of phosphonium salts, the generation of phosphorus ylides in solution can be complicated by undesirable side reactions. Consequently, phosphorus ylides must usually be prepared by means of meticulous, multiple-stage processes to avoid the preparation of the corresponding phosphonium salts (Aitken et al., *Phosphorus, Sulfur and Silicon* 101, 281 (1995)). Phosphorus ylides can sometimes react with the reaction solvent, thereby further complicating the synthesis. As a result, the choice of the reaction media is critical for both the generation of phosphorus ylides and in carrying out the Wittig-Horner reaction.

Environmental and health issues are other concerns with the use of organic solvents in the conventional preparation of phosphonium salts and phosphorus ylides. The reaction solvents can end up in waste streams, thereby straining the environment and causing health problems in the individuals exposed to them. Despite tremendous efforts directed towards the minimization of both environmental and health impacts of solvents, handling and elimination of solvents-related waste still remains one of the most difficult environmental and health problems. An effective approach to minimize the solvent-related chemical pollution is the replacement of solvents in both the industry and research laboratory by alternative materials acceptable from both environmental and health standpoints. However, a much more desirable method of resolving ecological problems caused by solvent wastes would be one that eliminates the use of solvents required for carrying out the particular chemical reactions altogether.

The present invention provides such a method. These and other advantages of the invention, as well as additional inventive features, will be apparent from the description of the invention provided herein.

BRIEF SUMMARY OF THE INVENTION

The invention provides a method of preparing a phosphonium salt of the formula $[R^1R^2R^3P{-}CR^4R^5R^6]X$, comprising ball-milling a phosphine of the formula $R^1R^2R^3P$ with a compound of the formula $XCR^4R^5R^6$; wherein $R^{1-3}$ are independently selected from the group consisting of hydrogen, $C_{1-25}$ alkyl, $C_{3-8}$ cycloalkyl, aralkyl, and aryl;

wherein $R^{4-6}$ are independently selected from the group consisting of hydrogen, $C_{1-25}$ alkyl, $C_{3-8}$ cycloalkyl, aralkyl, and aryl; and wherein X is a mono- or polyvalent anion. The invention further provides a method of preparing a phosphorus ylide of the formula $R^1R^2R^3P{=}CR^4R^5$, comprising ball-milling a phosphonium salt of the formula $[R^1R^2R^3P{-}HCR^4R^5]X$ (i.e., wherein $R^6$ is H) in the presence of a base; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion. A third aspect of the invention provides a method of preparing an olefin of the formula $R^4R^5C{=}CR^7H$ or $R^4R^5C{=}CR^7R^8$, comprising ball-milling a phosphorus ylide of the formula $R^1R^2R^3P{=}CR^4R^5$ with a compound of the formula $R^7C(O)H$ or $R^7C(O)R^8$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein $R^7$ and $R^8$ are independently selected from the group consisting of $C_{1-25}$ alkyl, $C_{3-8}$ cycloalkyl, aralkyl, or aryl.

The inventive method thus produces phosphonium salts, phosphorus ylides and olefins by means of mechanical processing of solid reagents under solvent-free conditions. The advantages of the present invention over the previously known, i.e. conventional solution methods, include: (1) extremely high selectivity of quaternization reactions and therefore, the relative absence of side products; (2) high yields; (3) low processing temperatures; (4) simple and scalable reactions using commercially available equipment; and (5) the complete elimination of solvents from the reaction course, thus allowing for a considerable reduction in the cost of the final product and, simultaneously, for a substantial reduction of chemical pollution caused by organic solvents. Furthermore, solvents may be needed only for separation and purification of reaction products, which allows avoidance of environmentally harmful liquids (e.g., toluene, benzene, hexane) and substitution with environmentally benign solvents such as water or supercritical $CO_2$.

DETAILED DESCRIPTION OF THE INVENTION

Figure 1:
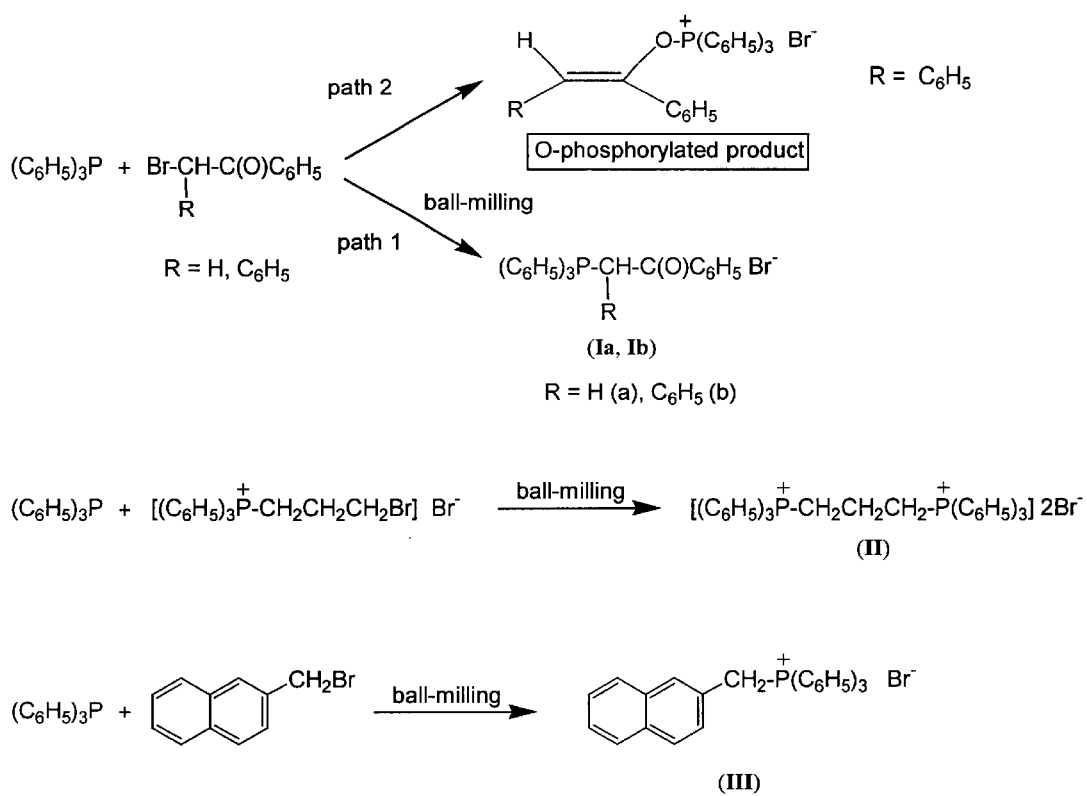
FIG. 1 schematically illustrates the preparation of phosphonium salts according to the present invention.

The invention provides a method of preparing a phosphonium salt of the formula $[R^1R^2R^3P{-}CR^4R^5R^6]X$. The method comprises ball-milling a phosphine of the formula $R^1R^2R^3P$ with a compound of the formula $XCR^4R^5R^6$; wherein $R^{1-3}$ are independently selected from the group consisting of hydrogen, $C_{1-25}$ alkyl, $C_{3-8}$ cycloalkyl, aralkyl, and aryl; wherein $R^{4-6}$ are independently selected from the group consisting of hydrogen, $C_{1-25}$ alkyl, $C_{3-8}$ cycloalkyl, aralkyl, and aryl; and wherein X is a mono- or polyvalent anion. The invention further provides a method of preparing a phosphorus ylide of the formula $R^1R^2R^3P{=}CR^4R^5$. The method comprises ball-milling a phosphonium salt of the formula $[R^1R^2R^3P{-}HCR^4R^5]X$ (i.e., wherein $R^6$ is H) with a base; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion. A third aspect of the invention provides a method of preparing an olefin of the formula $R^4R^5C{=}CR^7H$ or $R^4R^5C{=}CR^7R^8$. The method comprises ball-milling a phosphorus ylide of the formula $R^1R^2R^3P{=}CR^4R^5$ with a compound of the formula $R^7C(O)H$ or $R^7C(O)R^8$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein $R^7$ and $R^8$ are independently selected from the group consisting of $C_{1-25}$ alkyl, $C_{3-8}$ cycloalkyl, aralkyl, or aryl. Preferably, all of the above described methods and reactions take place in one reaction vessel (i.e., a "one pot" reaction).

The phosphonium salt, of the formula $[R^1R^2R^3P{-}CR^4R^5R^6]X$, is formed by ball-milling a phosphine of the formula $R^1R^2R^3P$ with a compound of the formula $XCR^4R^5R^6$. The substituents $R^{1-3}$ are independently selected from the group consisting of hydrogen, $C_{1-25}$ alkyl, $C_{3-8}$ cycloalkyl, aralkyl, and aryl; $R^{4-6}$ are independently selected from the group consisting of hydrogen, $C_{1-25}$ alkyl, $C_{3-8}$ cycloalkyl, aralkyl, and aryl; and X is a mono- or polyvalent anion.

For purposes of the present inventive methods, X can be any mono- (−1) or polyvalent (−2, −3, etc.) anion that forms a phosphonium salt. Representative examples of X include halides ($F^-$, $Cl^-$, $Br^-$, $I^-$), sulfate ($SO_4^{-2}$), sulfite ($SO_3^{-2}$), nitrate ($NO_3^{-1}$ phosphate ($PO_4^{-3}$), and carbonate ($CO_3^{-2}$). Preferably, X is a halide; more preferably X is $Cl^-$, $Br^-$, or $I^-$, and most preferably X is $Bra^-$.

The phosphonium salt produced by the present inventive method can be phenacyltriphenylphosphonium bromide, (α-benzoyl-α-phenylmethylene)-triphenylphosphonium bromide, propane-1,3-diyl-bis(triphenylphosphonium) dibromide, or (2-naphthalenylmethyl) triphenylphosphonium bromide, and the like.

In general, the phosphorus ylide, of the formula $R^1R^2R^3P=CR^4R^5$, is formed by ball-milling a phosphonium salt of the formula $[R^1R^2R^3P—HCR^4R^5]X$ in the presence of a base. The substituents $R^{1-3}$ are independently selected from the group consisting of hydrogen, $C_{1-25}$ alkyl, $C_{3-8}$ cycloalkyl, aralkyl, and aryl; $R^4$ and $R^5$ are independently selected from the group consisting of hydrogen, $C_{1-25}$ alkyl, $C_{3-8}$ cycloalkyl, aralkyl, and aryl; and X is a mono- or polyvalent anion, as described above. The ylide produced by the inventive method can be one of the major types of phosphorus ylides: stabilized, semistabilized, or nonstabilized. Typically stabilized ylides can be isolated and stored until use, whereas semistabilized and nonstabilized are preferably reacted with carbonyl compound in the Wittig-Horner reaction. The ylide produced can be benzoylmethylenetriphenylphosphorane, (α-benzoyl-α-phenylmethylene)triphenylphosphorane, or (carbethoxymethylene)-triphenylphosphorane, and the like.

The base used for the transformation of the phosphonium salt into the phosphorus ylide can be of any suitable strength. The amount and strength of the base will depend on the individual reactants, as is known. Typical bases include alkali metal carbonate ($M_2CO_3$), alkali metal hydroxides (MOH), alkali metal hydrides (ML), alkali metal alkoxides (M(OR), where R is $C_{1-6}$ alkyl), alkali metal amides ($M(NR_2)$, where R is hydrogen, $C_{1-6}$ alkyl or aryl), or any combination thereof. The alkali metal M preferably is Li, Na, K, Rb or Cs. A preferred base for use in the inventive method of preparing a phosphorous ylide is $K_2CO_3$.

In the present inventive method of preparing a phosphorous ylide, the phosphonium salt of formula $[R^1R^2R^3P—HCR^4R^5]X$ can be formed using a method comprising ball-milling a phosphine of the formula $R^1R^2R^3P$ with a compound of the formula $HCR^4R^5X$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion.

Figure 4:
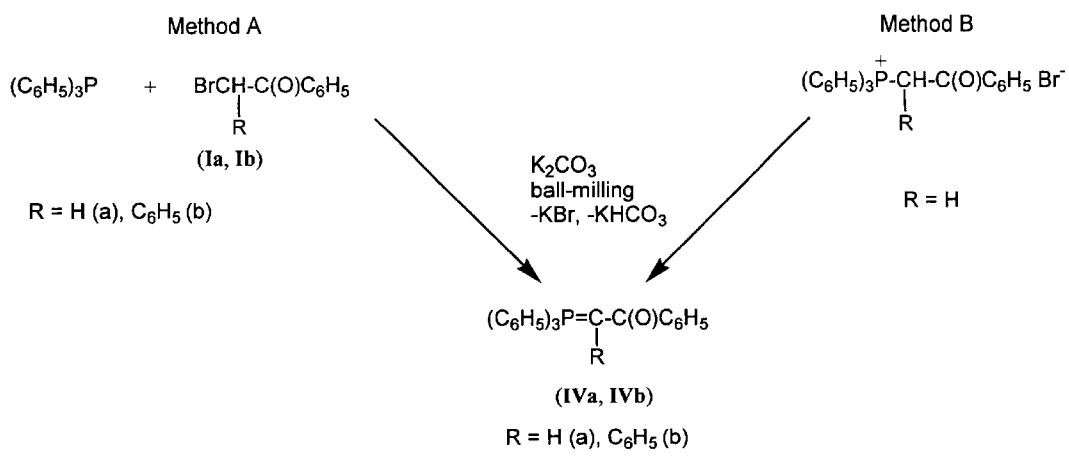
FIG. 4 schematically illustrates the preparation of phosphorus ylides according to the present invention, and carrying out the solvent-free Wittig-Horner reaction using such phosphorus ylides.
Figure 4:
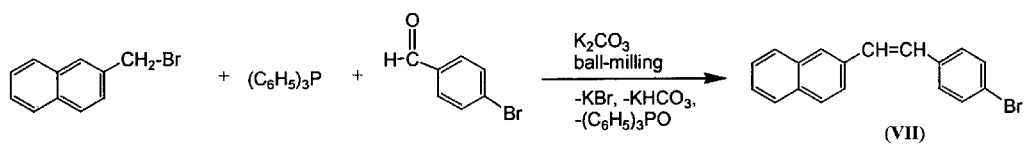
Figure 4:
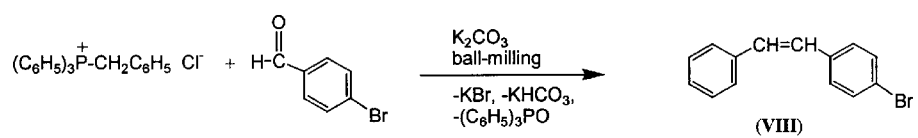

In the Wittig-Horner reaction, aldehydes and/or ketones are added to phosphorus ylides in order to produce olefinic products (FIG. 4). In the present invention, suitable aldehydes are of the formula: $R^7C(O)H$, and ketones are of the formula: $R^7C(O)R^8$. $R^7$ and $R^8$ are independently $C_{1-25}$ alkyl, $C_{3-8}$ cycloalkyl, aralkyl, or aryl. Preferably, the aldehyde or ketone is used in solid form.

The present invention provides a method of preparing an olefin compound of the formula $R^4R^5C=CR^7H$ or $R^4R^5C=CR^7R^8$. The method comprises ball-milling a phosphorus ylide of the formula $R^1R^2R^3P=CR^4R^5$ with a compound of the formula $R^7C(O)H$ or $R^7C(O)R^8$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein $R^7$ and $R^8$ are independently selected from the group consisting of $C_{1-25}$ alkyl, $C_{3-8}$ cycloalkyl, aralkyl, and aryl.

In the present inventive method of preparing an olefin compound, the phosphorous ylide of the formula $R^1R^2R^3P=CR^4R^5$ can be formed using a method comprising ball-milling a phosphonium salt of the formula $[R^1R^2R^3P—HCR^4R^5]X$ in the presence of a base; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion. The phosphonium salt of the formula $[R^1R^2R^3P—HCR^4R^5]X$ can be formed using the method comprising ball-milling a phosphine of the formula $R^1R^2R^3P$ with a compound of the formula $HCR^4R^5X$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion.

In this regard, the present invention provides a method of preparing an olefin compound of the formula $R^4R^5C=CR^7H$ or $R^4R^5C=CR^7R^8$. The method comprises: (a) ball-milling a phosphine of the formula $R^1R^2R^3P$ with a compound of the formula $HCR^4R^5X$; wherein $R^{1-3}$ are independently selected from the group consisting of hydrogen, $C_{1-25}$ alkyl, $C_{3-8}$ cycloalkyl, aralkyl, and aryl; wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion to provide a phosphonium salt reaction product of the formula $[R^1R^2R^3P—HCR^4R^5]X$; (b) ball-milling the phosphonium salt reaction product in the presence of a base to provide a phosphorus ylide reaction product of the formula $R^1R^2R^3P=CR^4R^5$, wherein $R^1$, $R^2$, $R^3$, $R^4$, and $R^5$ are as described above; (c) ball-milling the phosphorus ylide reaction product with a compound of the formula $R^7C(O)H$ or $R^7C(O)R^8$; wherein $R^7$ and $R^8$ are independently selected from the group consisting of $C_{1-25}$ alkyl, $C_{3-8}$ cycloalkyl, aralkyl, and aryl, to provide an olefin reaction product; and (d) isolating the olefin reaction product. This method of preparing an olefin can further comprise the step of isolating the phosphonium salt after step (a).

According to the methods of the present invention, the solid reaction components are subjected to a mechanical processing in the absence of a solvent at about −200° C. to about 100° C., preferably at about −100° C. to about 100° C., preferably from about −10° C. to about 75° C., preferably from about 0C to about 50° C., preferably from about 20° C. to about 40° C., and most preferably at ambient temperature (i.e., room temperature, about 25° C.). Preferably, the reaction takes place in a chemically inert atmosphere, preferably in an inert gas atmosphere (e.g., helium, neon, argon, nitrogen, and the like).

The reaction time depends on the nature of the reactants and can vary, in general, between about 0.01 hours to about 100 hours. Preferably, the reaction time is less than 100 h, more preferably the reaction time is less than 80 h, even more preferably the reaction time is less than 60 h, still even more preferably the reaction time is less than 40 h, further, more preferably the reaction time is less than 20 h, and even more preferably the reaction time is less than 10 h, less than 5 h, and even less than 2 h.

The mechanical processing can be carried out in any suitable apparatus, which delivers mechanical energy into the compounds located inside the apparatus, such as, for example, a shaker-type ball-mill, a planetary mill or an attritor mill. The milling equipment can be manufactured from typical materials such as metal, ceramics, minerals or glass. Specific examples of the milling equipment materials include steel and tungsten carbide. As used herein, the term "ball-milling" refers to processing using any such suitable apparatus for carrying out the desired mechanical processing.

After the mechanochemical processing is completed, the solvent-free synthesis products can be further processed as desired. Any purification scheme may be used if desired. As an illustrative example, following isolation, additional purification may be carried out by recrystallization from a suitable solvent, e.g., water, methanol or a methanol-hexane mixture.

While not wishing to be bound by any particular theory, several models describing mechanically induced reactions between phosphine and organic halides can be suggested. One probable mechanism when low-melting halides react with a phosphine (e.g., triphenylphosphine) is a local formation of low-melting eutectics in the phosphine—organic halide systems during ball-milling. In this instance, the reactions may occur in the melt, which forms locally and momentarily in the areas where the rapidly moving balls collide with both the walls of the reaction vessel and with one other. Alternatively, the reactions could occur as a sequence of solid-state processes, which include: (i) breaking the crystal lattice of a phosphonium compound and the formation of an amorphous phase; (ii) a deprotonation of an amorphous phosphonium salt by microcrystalline base (e.g., $K_2CO_3$) in a heterogeneous solid-state reaction.

Referring now to general terminology, as utilized generally herein, the term "alkyl" means a straight-chain or branched alkyl substituent containing from, for example, about 1 to about 25 carbon atoms, preferably from about 1 to about 12 carbon atoms, preferably from about 1 to about 8 carbon atoms, more preferably from about 1 to about 6 carbon atoms. Examples of such substituents include methyl, ethyl, propyl, iso-propyl, n-butyl, sec-butyl, iso-butyl, tert-butyl, n-pentyl, iso-amyl, hexyl, octyl, dodecanyl, and the like.

The term "cycloalkyl" refers to any substituted or unsubstituted cyclized hydrocarbon that is not considered aromatic. Preferably, the cycloalkyl contains about 3 to 8 carbons, preferably about 5 to 7 carbons, more preferably about 5 to 6 carbons, and most preferably about 6 carbons. The term cycloalkyl encompasses ring structures that are both saturated and unsaturated (i.e., single and/or double bonds). Specific examples of cycloalkyls include, for example, cyclopropyl, cyclopropenyl, cyclobutyl, cyclobutenyl, cyclopentyl, cyclopentenyl, cyclohexyl, cyclohexenyl, methcyclohexenyl, cycloheptyl, cycloheptenyl, cyclooctyl, and cyclooctenyl.

The term "aryl" refers to an unsubstituted or substituted aromatic carbocyclic substituent (i.e., those compounds that have 4n+2 pi electrons), as commonly understood in the art, and includes monocyclic and polycyclic aromatics such as, for example, phenyl and naphthyl substituents, and the like.

The term "aralkyl", as utilized herein, means alkyl as defined herein, wherein at least one hydrogen atom is replaced with an aryl substituent as defined herein. Aralkyls include, for example, benzyl, phenethyl, or substituents of the formula:

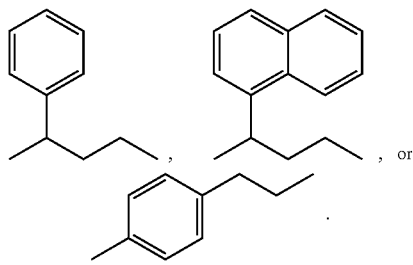

The following examples further illustrate the invention but, of course, should not be construed as in any way limiting its scope.

EXAMPLES

The reactants and reference compounds: triphenylphosphine, α-bromoacetophenone, 2-(bromomethyl)naphthalene, (benzyl) triphenylphosphonium chloride, (methyl) triphenylphosphonium bromide, (ethyl) triphenylphosphonium bromide, (2-naphthalenylmethyl) triphenylphosphonium bromide and 2-bromo-2-phenylacetophenone and aromatic aldehydes were purchased from Aldrich or otherwise specified. Other reactants and reference compounds: anhydrous $K_2CO_3$, phenacyltriphenylphosphonium bromide, 3-bromopropyl (triphenylphosphonium) bromide and propane-1,3-diyl-bis (triphenylphosphonium) dibromide were purchased from Lancaster Synthesis or otherwise specified. Solid state $^{-}P\{^1H\}$ CP MAS NMR spectra were recorded at room temperature on a Chemagnetics Infinity spectrometer operating at 400 MHz for $^1H$ and equipped with a double resonance Chemagnetics MAS probe. A variable amplitude approach to the CP MAS method was used (contact time=0.5 ms, relaxation delay=5 s, spinning rate=20 kHz). Liquid state $^1H$, $^{13}C$, and $^{31}P$ NMR spectra were obtained in $CDCl_3$ or $C_6D_6$ purchased from Cambridge Isotope Laboratories, Inc. using Varian VXR-300 and Varian VXR-400 spectrometers. Chemical shifts are reported with respect to $H_3PO_4$ in water (85% solution) ($^{31}P$) or to tetramethylsilane ($^1H$ and $^{13}C$) as the external standards. The X-ray powder diffraction experiments were performed on a Scintag diffractometer using Cu $K_\alpha$ radiation.

Ball-milling (usually about 1.0 g total material) was performed in a Spex 8000 mill using 21 g of steel balls in a hardened-steel vial, or 70 g of tungsten carbide balls in a tungsten carbide vial (when higher input of mechanical energy was desired) sealed under helium. Forced-air cooling of the vials was employed to prevent their heating during the ball-milling experiments. No heating of the milling equipment was detected during mechanical treatment.

Example 1

This example describes the preparation of phenacyltriphenylphosphonium bromide (Ia), FIG. 1.

Ia was prepared from 0.70 g (2.7 mmol) of triphenylphosphine and 0.53 g (2.7 mmol) of α-bromoacetophenone by ball-milling for one hour under helium. The resulting powder was analyzed by solid state $^{31}P\{^1H\}$ CP MAS NMR spectroscopy, and the salt Ia was re-crystallized from water for an additional purification. Yield: 1.10 g (90%).

Mechanochemically prepared phenacyltriphenylphosphonium bromide (Ia): solid state $^{31}P\{^1H\}$ CP MAS NMR: $\delta^{31}P$ (ppm): 23.0; liquid state NMR (CDCl$_3$): $\delta^{31}$P (ppm): 23.0; $\delta^1$H/J$_{P-H}$ (ppm/Hz): 8.38/7.4 (d, 2H, Ph), 8.01–7.90 (m, 6H, Ph), 7.67–7.74 (m, 4H, Ph), 7.67–7.54 (m, 6H, Ph), 7.52–7.45 (m, 2H, Ph), 6.40/12.2 (d, 2H, CH$_2$); 270–273° C.

Phenacyltriphenylphosphonium bromide (compound Ia in FIG. 1) was also purchased and used as a reference. Commercial phenacyltriphenylphosphonium bromide (Lancaster Synthesis): solid state $^{31}$P{$^1$H} CP MAS NMR: $\delta^{31}$P (ppm): 23.0; liquid state NMR (CDCl$_3$): $\delta^{31}$P (ppm): 23.0; $\delta^1$H/J$_{P-H}$ (ppm/Hz): 8.38/7.4 (d, 2H, Ph), 8.01–7.90 (m, 6H, Ph), 7.67–7.75 (m, 4H, Ph), 7.67–7.55 (m, 6H, Ph), 7.52–7.45 (m, 2H, Ph), 6.40/12.2 (d, 2H, CH$_2$); Mp 268–270° C.

Figure 2:
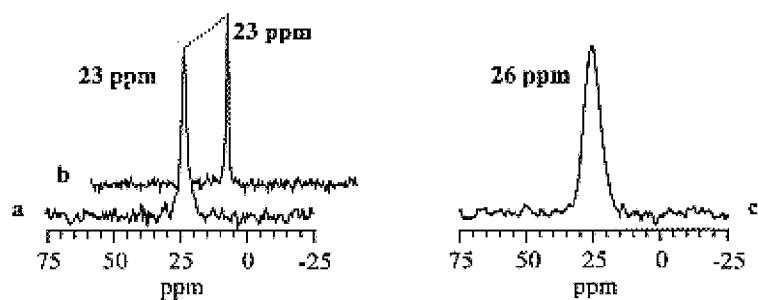
FIG. 2 depicts the solid state $^{31}P$ {$^1H$} CP MAS NMR spectra of (a) mechanochemically prepared phenacyltriphenylphosphonium bromide (Ia), (b) the conventionally synthesized salt purchased from Lancaster Synthesis, and (c) (α-benzoyl-α-phenylmethylene)triphenylphosphonium bromide (Ib) prepared mechanochemically.
Figure 3:
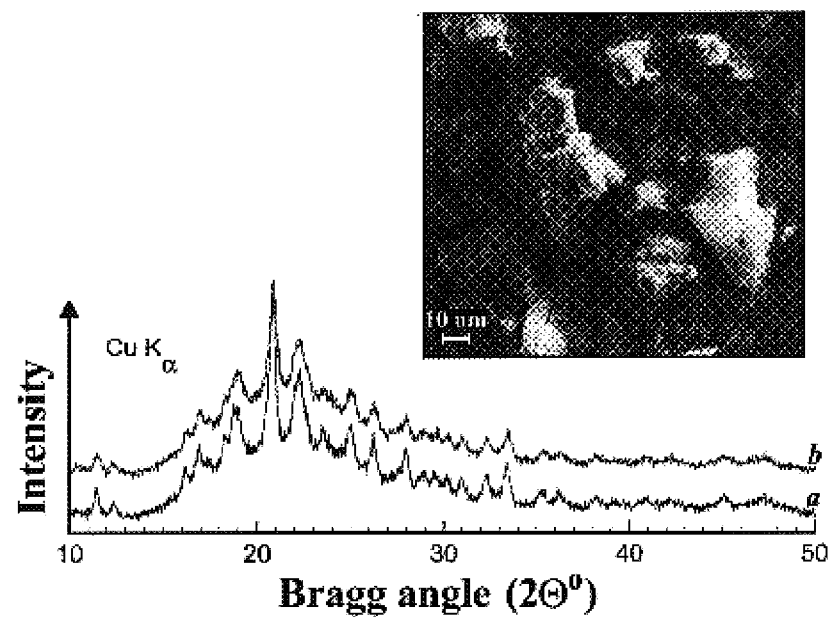
FIG. 3 depicts the X-ray powder diffraction patterns, obtained using Cu $K_\alpha$-radiation, of (a) phenacyltriphenylphosphonium bromide (Ia) prepared mechanochemically by ball-milling of triphenylphosphine and α-bromoacetophenone for one hour without a solvent, and (b) commercial phenacyltriphenylphosphonium bromide (Lancaster) ball-milled for one hour under helium to achieve comparable particle size distribution and similar degree of crystallinity as in Ia. The SEM micrograph of the product Ia is shown in the inset.

The solid state $^{31}$P{$^1$H} CP MAS NMR spectra of both the powder obtained during mechanical processing and the commercial phosphonium salt are shown in FIGS. 2a and 2b, respectively. Both contain only one signal at the chemical shift $\delta^{31}$P=23 ppm indicating a complete transformation of triphenylphosphine and α-bromoacetophenone into phenacyltriphenylphosphonium bromide. In addition, the X-ray powder diffraction pattern of the compound prepared mechanochemically in a solid state was compared with that of the commercial (i.e., conventionally prepared in a solution) phosphonium salt that was ball-milled for one hour under helium to achieve similar particle size, concentration of defects and level of strain in both products (FIGS. 3a and 3b). The $^{31}$P{$^1$H} CP MAS NMR spectra and the X-ray diffraction patterns of both solids are in an excellent agreement. The SEM micrograph of the powder obtained after ball-milling of triphenylphosphine and α-bromoacetophenone is shown in the inset of FIG. 3.

Example 2

This example illustrates the synthesis of (α-benzoyl-α-phenylmethylene)triphenylphosphonium bromide (Ib), FIG. 1. It was reported previously that 2-bromo-2-phenylacetophenone reacts with triphenylphosphine in a solution following both path 1 and 2 shown in FIG. 1, thus yielding a mixture of C- and O-phosphorylated reaction products (Borowitz et al., *J. Org. Chem.* 34, 1595 (1969)). As a result, (α-benzoyl-α-phenylmethylene)triphenylphosphonium bromide (compound Ib in FIG. 1) is difficult to separate from by-products. The corresponding ylide ((α-benzoyl-α-phenylmethylene)triphenylphosphorane) is, therefore, usually prepared in a lengthy multiple step process which avoids the use of (α-benzoyl-α-phenylmethylene)triphenylphosphonium salts (Sanz, *J. Carbohydr. Chem.* 17, 1331 (1998)).

The salt Ib was prepared from 0.42 g (1.6 mmol) of triphenylphosphine and 0.44 g (1.6 mmol) 2-bromo-2-phenylacetophenone by ball-milling for one hour under helium. The sample for the liquid state NMR investigations and the elemental analysis was re-crystallized from a methanol-diethyl ether solution for an additional purification and dried under vacuum. Yield: 0.61 g (99%).

The solid state $^{31}$P NMR spectrum of the ball-milled sample contains only one peak centered at $\delta^{31}$P=26 ppm, consistent with the position of the signal in the NMR spectrum of pure (α-benzoyl-α-phenylmethylene) triphenylphosphonium bromide (FIG. 2c). The latter was obtained in a crystalline form by re-crystallization of the mechanochemically prepared sample from a methanol-diethyl ether solution and characterized by $^1$H, $^{31}$P, and $^{13}$C NMR spectroscopy in a CDCl$_3$ solution, and elemental analysis.

Mechanochemically prepared (α-benzoyl-α-phenylmethylene) triphenylphosphonium bromide (Ib): solid state $^{31}$P{$^1$H} CP MAS NMR: $\delta^{31}$P (ppm): 26.0; liquid state NMR (CDCl$_3$): $\delta^{31}$P (ppm): 27.4; $\delta^1$H/J$_{P-H}$ (ppm/Hz): 9.30/12.4 (d, 1H, CH), 8.42 (m, 2H, Ph), 8.02–7.96 (m, 6H, Ph), 7.71–7.67 (m, 3H, Ph), 7.60-7.55 (m, 6H, Ph), 7.46–7.35 (m, 5H, Ph), 7.22–7.19 (m, 1H, Ph), 7.15–7.11 (m, 2H, Ph); $\delta^{13}$C{$^1$H}/J$_{C-P}$ (ppm/Hz): 195.36/3.6 (d, CO), 135.57/9.7 (d, Ph), 134.41 (m, Ph), 133.78/5.2 (d, Ph), 131.89/5.2 (d, Ph), 131.19 (s, Ph), 129. 75/13.2 (d, Ph), 129.51/2 (d, Ph), 129.17/2 (d, Ph), 128.86 (s, Ph), 128.83/5.9 (d, Ph), 118.78/86.6 Hz (d, CP, Ph), 54.30/54.9 (d, CP).

Found (%): C 70.74%, H 5.19. Calculated for C$_{32}$H$_{26}$OPBr (%): C 71.50, H 4.84%; Mp 246–248° C. (decomposition).

Example 3

This example describes the preparation of propane-1,3-diyl-bis(triphenylphosphonium) dibromide (II), FIG. 1.

0.83 g (3.2 mmol) of triphenylphosphine and 0.50 g (1 mmol) of 3-bromopropyl(triphenylphosphonium) bromide were ball-milled in a tungsten carbide vial using 70 g of tungsten carbide balls for 12.5 hours. The resulting powder was analyzed by the solid state NMR spectroscopy, which confirmed the formation of the salt II, then treated with 100 ml of chloroform, filtered, and the solvent was removed under vacuum. The compound II was isolated in 51% yield (0.40 g) and additionally purified by re-crystallization from a methanol-hexane mixture.

Mechanochemically prepared propane-1,3-diyl-bis (triphenylphosphonium) dibromide (II): liquid state NMR (CDCl$_3$): $\delta^{31}$P (ppm): 25.4; $\delta^1$H (ppm): 7.87–7.83 (m, 10H, Ph), 7.71–7.57 (m, 20H, Ph), 4.64–4.55 (m, 4H, CH$_2$), 2.3–1.83 (m, 2H, CH$_2$). Mp 355–360° C. (decomposition).

Commercial propane-1,3-diyl-bis (triphenylphosphonium) dibromide (Lancaster Synthesis) was compared to the mechanochemically-prepared sample. Liquid state NMR (CDCl$_3$): $\delta^{31}$P (ppm): 25.4; $\delta^1$H/J$_{P-H}$ (ppm): 7.90–7.83 (m, 10H, Ph), 7.70–7.55 (m, 20H, Ph), 4.64–4.55 (m, 4H, CH$_2$), 2.3–1.84 (m, 2H, CH$_2$). Mp>300° C. (decomposition).

Example 4

This example illustrates the preparation of (2-naphthalenylmethyl)-triphenylphosphonium bromide (III), FIG. 1.

0.40 g (1.5 mmol) of triphenylphosphine and 0.34 g (1.5 mmol) of 2-(bromomethyl)naphthalene were ball-milled for 1 hour under helium. The resulting powder was analyzed by the solid state $^{31}$P{$^1$H} CP MAS NMR spectroscopy, which confirmed the formation of III, and the compound III was re-crystallized from methanol for an additional purification. Yield: 0.70 g (95%).

Mechanochemically prepared (2-naphthalenylmethyl) triphenylphosphonium bromide (III): liquid state NMR (CDCl$_3$): $\delta^{31}$P (ppm): 24.4; $\delta^1$H/J$_{P-H}$ (ppm): 7.98–7.1 (m, 22H, Aryl), 5.6/12.4 (d, 2H, CH$_2$). Mp 239–241° C.

Commercial (2-naphthalenylmethyl) triphenylphosphonium bromide (Aldrich) was compared to the mechanochemically-prepared sample: NMR (CDCl$_3$): $\delta^{31}$P (ppm): 24.7; $\delta^1$H/J$_{P-H}$ (ppm): 8.0–7.1 (m, 22H, Aryl), 5.6/12.4 (d, 2H, CH$_2$). Mp 237–240° C.

Example 5

This example illustrates the preparation of benzoylmethylenetriphenylphosphorane (IVa), FIG. 4.

Method A 0.70 g (2.7 mmol) of triphenylphosphine and 0.53 g (2.7 mmol) of α-bromoacetophenone were ball-milled for one hour, then the vial was opened in a glove box under helium and 0.53 g (3.84 mmol) of $K_2CO_3$ were added to the reaction mixture. The vial was resealed and ball-milling continued for an additional three hours. The ylide IVa was isolated in 99% yield (0.65 g) by dissolution of the reaction mixture in toluene, filtration, and evaporation of the solvent.

Method B 0.70 g (1.5 mmol) of phenacyltriphenylphosphonium bromide and 0.25 g (1.8 mmol) of anhydrous $K_2CO_3$ were ball-milled for three hours. The resulting powder was analyzed by both solid state $^{31}P\{^1H\}$ CP MAS NMR spectroscopy and X-ray powder diffraction, then treated with 40 ml of toluene, filtered, and the solvent was removed by distillation under vacuum. The ylide IVa was obtained in 99% yield (0.56 g).

Figure 6:
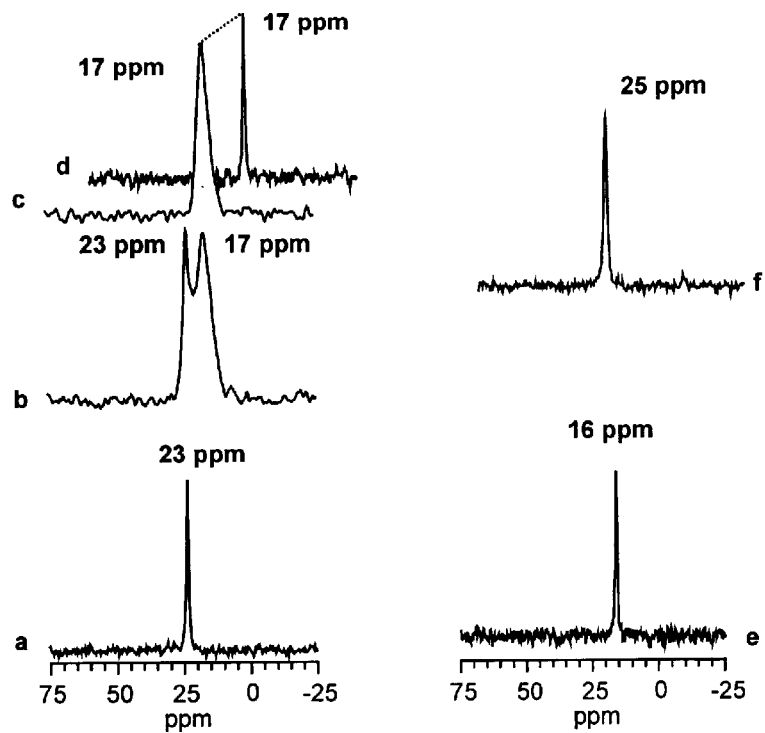
FIG. 6 depicts the solid state $^{31}P$ {$^1H$} CP MAS NMR spectra of (a) phenacyltriphenylphosphonium bromide (Ia); (b) the reaction mixture obtained after ball-milling of phenacyltriphenylphosphonium bromide (Ia) with anhydrous $K_2CO_3$ for one hour; (c) the reaction mixture obtained after ball-milling of phenacyltriphenylphosphonium bromide (Ia) with anhydrous $K_2CO_3$ for three hours; (d) the commercial benzoylmethylenetriphenylphosphorane; (e) (α-benzoyl-α-phenylmethylene)triphenylphosphorane (IVb) prepared mechanochemically; (f) the reaction mixture obtained after ball-milling triphenylphosphine, 2-(bromometyhl) naphthalene and p-bromobenzaldehyde in the presence of potassium carbonate.

The spectra of the reaction mixtures formed after mechanical treatment and that of the commercial ylide are shown in FIGS. 6b, 6c, and 6d, respectively. The spectrum of the sample obtained after ball-milling for one hour consists of two peaks at the chemical shift $\delta^{31}P=23$ and 17 ppm (FIG. 6b). The peak at $\delta^{31}P=23$ ppm corresponds to the starting phenacyltriphenylphosphonium bromide (FIG. 6a) remaining in the reaction mixture after one hour of ball-milling. The location of the second peak at $\delta^{31}P=17$ ppm is the same as the signal in the solid state $^{31}P\{^1H\}$ CP MAS NMR spectrum of the commercial benzoylmethylenetriphenylphosphorane (FIG. 6d). After ball-milling for three hours, the solid state NMR spectrum of the reaction mixture (FIG. 6c) contains only one peak at $\delta^{31}P=17$ ppm indicating a complete transformation of phenacyltriphenylphosphonium bromide into the benzoylmethylenetriphenylphosphorane (IVa).

Figure 7:
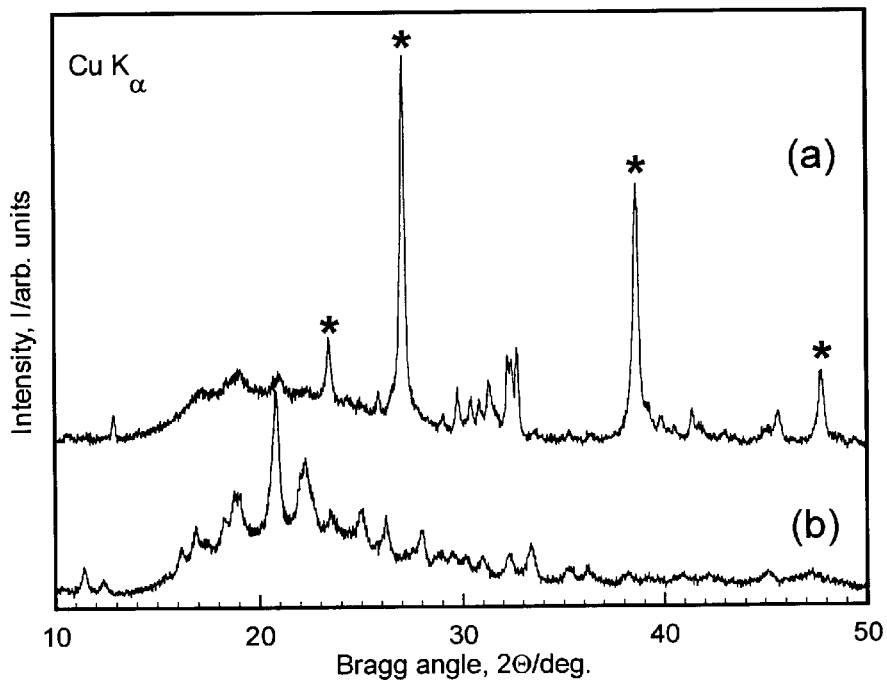
FIG. 7 depicts the X-ray powder diffraction patterns of (a) the reaction mixture obtained after ball-milling phenacyltriphenylphosphonium bromide (Ia) with anhydrous $K_2CO_3$; and (b) the pure mechanically treated phenacyltriphenylphosphonium bromide (Ia). Asterisks indicate Bragg peaks corresponding to potassium bromide.

The X-ray powder diffraction analysis (FIG. 7) also confirms the completion of the transformation during ball-milling. The X-ray powder diffraction pattern of the powder sample after mechanical processing contains strong Bragg peaks of potassium bromide (KBr), which is one of the expected reaction products, and a set of peaks corresponding to micro/nano-crystalline phases completely different from that of the starting compounds.

Mechanochemically prepared benzoylmethylenetriphenylphosphorane: solid state $^{31}P\{^1H\}$ CP MAS NMR: $\delta^{31}P$ (ppm): 17.0; liquid state N (CDCl$_3$): $\delta^{31}P$ (ppm): 18.3; $\delta^1H/J_{P-H}$ (ppm/Hz): 8.38/8.1, 1.5 (dd, 2H, Ph), 7.74 (m, 6H, Ph), 7.24 (m, 6H, Ph), 7.00 (m, 6H, Ph), 4.56/25.7 (d, 1H, CH); Mp 178–183° C.

Commercial benzoylmethylenetriphenylphosphorane (Alfa Aesar) was compared to the product prepared by Methods A and B: solid state $^{31}P\{^1H\}$ CP MAS NMR: $\delta^{31}P$ (ppm): 17.0; liquid state NMR (CDCl$_3$): $\delta^{31}P$ (ppm): 18.3; $\delta^1H/J_{P-H}$ (ppm/Hz): 8.37/8.1, 1.5 (dd, 2H, Ph), 7.77–7.70 (m, 6H, Ph), 7.26–7.22 (m, 6H, Ph), 7.04–6.93 (m, 6H, Ph), 4.56/25.3 (d, 1H, CH); Mp 182–185° C.

Example 6

This example illustrates the preparation of (α-benzoyl-α-phenylmethylene)-triphenylphosphorane (IVb), FIG. 4.

0.60 g (2.29 mmol) of triphenylphosphine and 0.63 g (2.29 mmol) of 2-bromo-2-phenylacetophenone were ball-milled for one hour, then the vial was opened in a glove box under helium, and 0.5 g (3.62 mmol) of $K_2CO_3$ was added to the reaction mixture. The vial was resealed and ball-milling continued for additional three hours. The formation of IVb was confirmed by the solid state $^{31}P$ NMR spectroscopy. The phosphorane IVb was isolated by dissolution of the solid reaction mixture in toluene, filtration, and evaporation of the solvent. Yield 1.0 g (99%).

(α-benzoyl-α-phenylmethylene)triphenylphosphorane: solid state $^{31}P\{^1H\}$ CP MAS NMR: $\delta^{31}P$ (ppm): 16.0; liquid state NMR (CDCl$_3$): $\delta^{31}P$ (ppm): 16.64 {lit. (Aitken et al., Phosphorus, Sulfur and Silicon 101,281 (1995))$\delta^{31}P$=16.0 ppm}; $\delta^1H$ (ppm): 7.63–7.56 (m, 6H, Ph), 7.47–7.40 (m, 11H, Ph), 7.09–7.06 (m, 3H, Ph), 6.86 (s, 5H, Ph); $\delta^{13}C\{^1H\}/J_{C-P}$ (ppm/Hz): 184.10/5.0 (d, CO), 141.35/11.5 (d, Ph), 138.91/11.5 (d, Ph), 137.75/4.6 (d, Ph), 133.45/9.6 (d, Ph), 131.19/2.6 (d, Ph), 128.95 (s, Ph), 128.35/12.2 (d, Ph), 128.13 (s, Ph), 127.30/1.9 (d, Ph), 127.10/90.8 (d, CP, Ph), 126.96 ppm(s, Ph), 124.65/2.7 (d, Ph), 72.90/109.1 (d, CP); MS (70 eV, EI): m/z (%): 456 (100) [M$^+$], 379 (15) [M$^+$-C$_6$H$_5$], 262 (12) [(C$_6$H$_5$)$_3$P$^+$], 183 (15); 178 (33), 165 (15); Mp 192–194° C. {lit.: 192–194° C. (Aitken et al., Phosphorus, Sulfur and Silicon 101, 281 (1995))}.

Example 7

Figure 5:
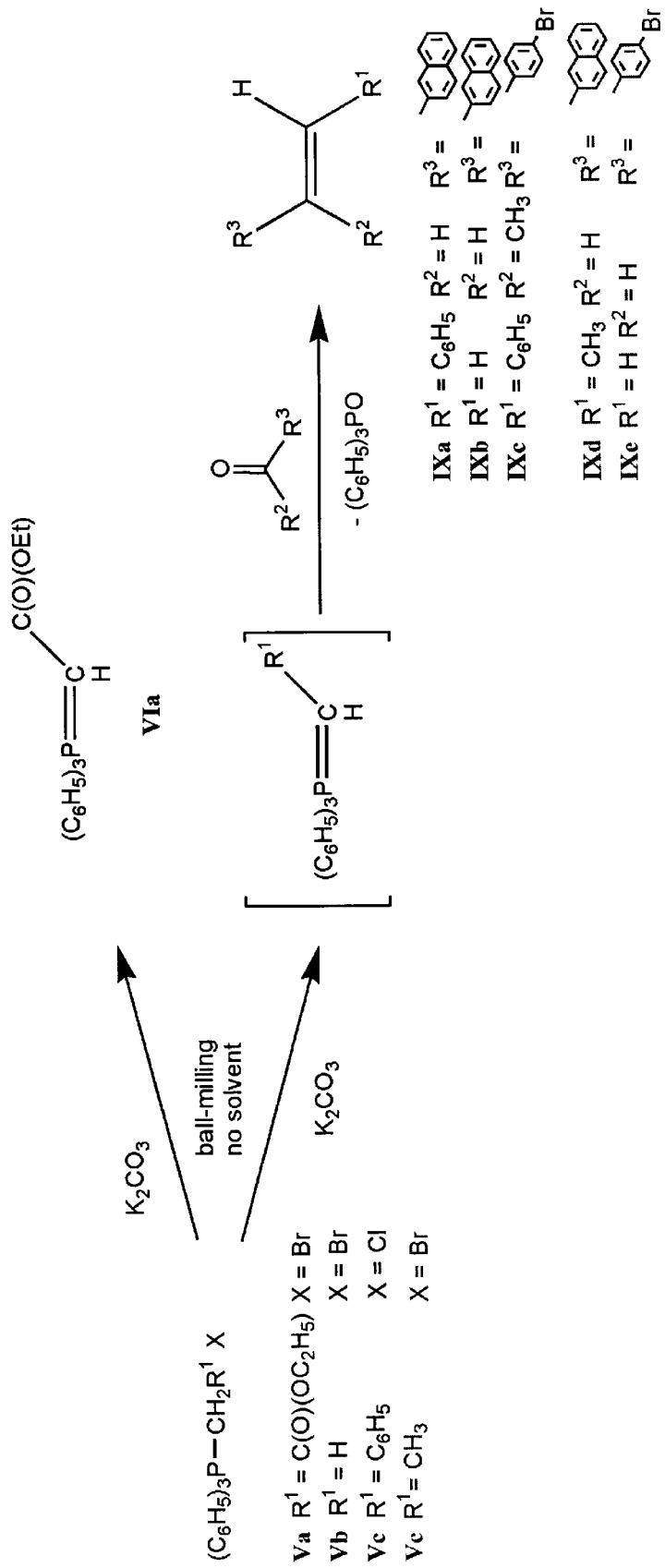
FIG. 5 schematically illustrates the preparation of phosphorus ylides according to the present invention, and carrying out the solvent-free Wittig-Horner reaction using such phosphorus ylides.

This example describes the preparation of (carbethoxymethylene)-triphenylphosphorane (VIa), FIG. 5.

(Carbethoxymethylene)triphenylphosphorane (VIa) was prepared from 3.0 g (6.98 mmol) of (carbethoxymethylene)triphenylphosphonium bromide (Va) and 2.0 g (14.49 mmol) of anhydrous $K_2CO_3$ during mechanical processing for four hours. The completion of the reaction was confirmed by the solid state $^{31}P$ MAS NMR spectroscopy. After dissolving the ball-milled powder in toluene and filtration, the ylide VIa was isolated in 96% yield (2.34 g).

(Carbethoxymethylene)triphenylphosphorane (VIa). Solid state $^{31}P$ MAS NMR: $\delta^{31}P$ (ppm): 1; liquid state NMR (C$_6$D$_6$): $\delta^{31}P$ (ppm): 19.3 {lit.: $\delta^{31}P$=17.9 ppm (Climent et al., J. Org. Chem. 54, 3695 (1989))}; $\delta^1H/J_{P-H}$ (ppm/Hz): 7.69–7.58 (m, 6H, Ph), 7.07–6.95 (m, 9H, Ph), 4.43/7 (q, 2H, CH$_2$), 3.34/23.8 (d, 1H, CH), 1.25/7 (t, CH$_3$); $\delta^{13}C\{^1H\}/J_{C-P}$ (ppm/Hz): 172.4/14 (d, CO), 141.35/11.5 (d, Ph), 138.91/11.5 (d, Ph), 133.70/9.9 (d, Ph), 132.05/2.3 (d, Ph), 129.95 (s, Ph), 129.09/11.8 (d, Ph), 58.34 (s, Et), 30.16/30.1 (d, CH), 15.96 (s, Et) {lit.: liquid state NMR (CDCl$_3$): $\delta^1H/J_{P-H}$ (ppm/Hz): 8.0–7.3 (m, Ph), 3.99/7 (q, CH$_2$), 2.91 (br, CH), 1.07/7 (t, CH$_3$) (Weleski et al., J. Organomet. Chem. 102, 365 (1975))}; MS (70 eV, EI) m/z (%): 347 (60) [M$^+$], 319 (27) [M$^+$-Et], 303 (52) [M$^+$-OEt], 275 (100), 196 (12) 183 (4), 165 (8); Mp 125–128° C. {lit.: m.p. 125–127.5° C. (Kolodiazhny, Phosphorus ylides, Wiley-VCH, Weincheim, 1999)}.

Example 8

This example describes the preparation of 1-(p-bromophenyl)-2-(naphthyl)ethylene (VII), FIG. 4.

0.50 g (1.91 mmol) of triphenylphosphine, 0.42 g (1.90 mmol) of 2-bromomethylnaphthalene, 0.36 g (1.98 mmol) of p-bromobenzaldehyde, and 0.50 g (3.62 mmol) of $K_2CO_3$ were placed in a hardened-steel vial in a glove box under helium. The vial was sealed, and the sample was ball-milled for eight hours. The formed powder was first analyzed by solid state $^{31}P\{^1H\}$ CP MAS NMR spectroscopy, then loaded on a silica gel chromatography column, and the mixture of (E)- and (Z)-1-(p-bromophenyl)-2-(naphthyl) ethylenes (VII) (E:Z ratio ca. 3.5:1 by $^1H$ NMR in CDCl$_3$) was isolated in 93% yield, (0.54 g ) by eluation with hexane and toluene. Triphenylphosphine oxide was further obtained from the same column in 92% yield (0.53 g) using a hexane-acetone mixture as an eluant. The separation and purification of the E-isomer was performed according to the previously described procedure (Brooks et al., J. Am. Chem. Soc. 121, 5444 (1999)) by the column chromatography on silica gel.

The solid state $^{31}P\{^1H\}$ CP MAS NMR spectrum of the obtained powder contained only one peak at $\delta^{31}P=25$ ppm (FIG. 5e), which corresponds to the position of the signal in the solid state $^{31}P$ NMR spectrum of triphenylphosphine oxide (Arumugam et al, *J. Chem. Soc., Chem. Comm.* 724 (1992)). Also, the $^{31}P$ and $^1H$ NMR spectroscopy in the solution (CDCl$_3$) confirmed the completion of the reaction as shown in FIG. 4. The (E)- and (Z)-isomers of VII in the reaction mixture formed in a 3.5:1 ratio as determined from the $^1H$ NMR spectrum in CDCl$_3$. Thus, the mechanochemical reaction is considerably more selective when compared with the similar process in the solution, where trans to cis ratio was found to be approximately 0.4:1 (Brooks et al., *J. Am. Chem. Soc.* 121, 5444 (1999)).

(E)-1-(p-Bromophenyl)-2-(naphthyl)ethylene (VII): liquid state NMR (CDCl$_3$): $\delta^1H/J_{H-H}$ (ppm/Hz): 7.85–7.77 (m, 4H, Ph), 7.72/8.8, 1.7 (dd, 1H, Ph), 7.51–7.40 (m, 6H, Ph), 7.26/14, 7.16/14 (dd, 2H, CH); $\delta^{13}C\{^1H\}$ (ppm) :136.51, 134.63, 133.86, 133.34, 132.04, 129.69, 128.62, 128.24, 128.20, 127.93, 127.09, 126.64, 126.29, 123.57, 121.58; MS (70 eV, EI): m/z (%): 308/310 (100/88) [M$^+$], 229 (51) [M$^+$-HBr], 228 (91) [M$^+$-2H-Br], 202 (15), 128 (10) [C$_{10}$H$_8^+$], 114 (55); 101 (29); Mp 186–189° C. {lit.: 188.5–189° C. (Brooks et al., *J. Am. Chem. Soc.* 121, 5444 (1999))}.

Triphenylphosphine oxide: solid state $^{31}P$ MAS NMR: $\delta^{31}P$ (ppm): 25; liquid state NMR (CDCl3): $\delta^{31}P$ (ppm): 30.2; $\delta^1H$ (ppm): 7.70–7.63 (m 6H, Ph), 7.56–7.42 (m, 12H, Ph), $\delta^{13}C\{^1H\}/J_{C-P}$ (ppm) 133.22, 132.13, 132.00, 131.93, 131.84, 128.55 128.39; Mp 155–57° C. {lit.: 152–153, 157° C. (*The Aldrich library of $^{13}C$ and $^1H$ FT NMR spectra, Ed. I*, Eds.: C. J. Pouchert, J. Behnke, Aldrich Chemical Company, Inc. p. 1691, 1993)}.

Example 9

This example illustrates the preparation of 4-bromostilbene (VIII) in situ from (benzyl) triphenylphosphonium chloride, K$_2$CO$_3$, and p-bromobenzaldehyde, FIG. 4.

0.70 g (180 mmol) of (benzyl)triphenylphosphonium chloride, 0.33 g (1.80 mmol) of p-bromobenzaldehyde and 0.50 g (3.62 mmol) of K$_2$CO$_3$ were placed into a hardened-steel vial in a glove box under helium. The vial was sealed in helium atmosphere and the sample was ball-milled for eight hours. The formed powder was first analyzed by the solid- and liquid state NMR spectroscopy, then loaded on a silica gel chromatography column, and the mixture of (E)- and (Z)-4-bromostilbenes (VIII) was isolated by eluation with hexane and toluene (E:Z ratio ca. 2:1 by $^1H$ NMR in CDCl$_3$) in 90% yield (0.45 g). Triphenylphosphine oxide was further obtained from the same column in 90% yield (0.44 g) using a hexane-acetone mixture as an eluant.

(E)-4-Bromostilbene (VIII): liquid state NMR (CDCl$_3$): $\delta^1H/J_{H-H}$ (ppm/Hz): 7.5–7.44 (m, 4H, Ph), 7.37–7.33 (m, 4H, Ph), 7.28–7.21 (m, 1H, Ph) 7.08/16.3. 7.01/16.3 (dd, 2H, CH); $\delta^{13}C\{^1H\}$ (ppm):137.11, 136.44,131.95, 129.58, 128.92, 128.15, 128.08, 127.65, 126.74, 121.49; MS (70 eV, EI): m/z (%): 260/258 (99/98) [M$^+$], 179 (37) [M$^+$-Br], 178 (100) [M$^+$-HBr], 151 (10), 89 (15) 76 (7); Mp 132-135° C. {lit.: 132–133° C. (Kumari et al., *J. Organometallic Chem.* 96, 237 (1975); Christoforou et al., *Aust. J. Chem.* 35, 729-(1982))}.

Example 10

This example illustrates the preparation of 1-(phenyl)-2-(naphthyl)ethylene (IXa), FIG. 5.

0.90 g (2.31 mmol) of (benzyl)triphenylphosphonium chloride (Vc), 0.36 g (2.31 mmol) of 2-naphthaldehyde and 0.60 g (4.35 mmol) of anhydrous K$_2$CO$_3$ were placed into a hardened-steel vial in a glove box under helium. The vial was sealed in helium atmosphere and the sample was ball-milled for seven hours. The formed powder was first analyzed by the solid state $^{31}P$ MAS NMR spectroscopy, which revealed one signal corresponding to triphenylphosphine oxide at $\delta^{31}P=25$ ppm. 1.7 g of the powder was loaded on the top of a silica-gel filled chromatographic column, and the mixture of (E)- and (Z)-1-(phenyl)-2-(naphthyl) ethylenes (IXa) was isolated by eluation with a hexane— toluene mixture in 85% yield, (0.41 g ). Triphenylphosphine oxide was further obtained from the same column in 82% yield (0.48 g) using a hexane-acetone mixture as an eluant. The partial separation of the E-isomer (0.25 g) was accomplished by the column chromatography on silica gel. Based on the amounts of isolated products, E/Z-isomer ratio was estimated to be at least 1.6:1.

(E)-1-(phenyl)-2-(naphthyl)ethylene (IXa): Liquid state NMR (CDCl$_3$): $\delta^1H/J_{H-H}$ (ppm/Hz): 7.82–7.78 (m, 4H), 7.72/8.4 (d, 1H), 7.54/8.2 (d, 2H), 7.74–7.37 (m, 4H), 7.28–7.18(m, 3H); $\delta^{13}C\{^1H\}$ (ppm): 137.27, 134.74, 133.63, 132.97, 128.95, 128.69, 128.65, 128.23, 127.93, 127.62, 126.57, 126.48, 126.26, 125.82, 123.44 (lit. (Brooks et al., *J. Am. Chem. Soc.* 121, 5444 (1999)): liquid state NMR (CDCl$_3$): $\delta^1H/J_{H-H}$ (ppm): 7.87–7.80 (m, 4H), 7.72/8.4, 1.6 (dd, 1H), 7.54/8.2 1.0 (dd, 2H), 7.45/6.7, 1.7 (td, 1H), 7.39/7.6 (t, 2H), 7.30/16 (d, 1H), 7.29/7.2, 1.6 (dt, 1H,), 7.24/16.4 (d, 1H); $\delta^{13}C\{^1H\}$ (ppm): 137.57, 135.03, 133.92, 133.25, 129.24, 128.94, 128.53, 128.21, 127.90, 126.84, 126.76, 126.55, 126.11, 123.71}; MS (70 eV, EI) m/z (%): 230 (100) [M$^+$], 215 (5), 202 (1.8), 152 (1) 114 (2); Mp 145–148° C. {lit.: 147–148° C. Brooks et al., *J. Am. Chem. Soc.* 121, 5444 (1999)}.

(Z)-1-(phenyl)-2-(naphthyl)ethylene (IXa): Liquid state NMR (CDCl$_3$, after extraction of the signals of the E-isomer): $\delta^1H/J_{H-H}$ (ppm/Hz): 7.74–7.67 (m, 2H), 7.61/8.5 (d, 1H), 7.47–7.38 (m, 2H), 7.54/8.5 1.2 (dd, 1H) 7.28–7.25 (m, 2H), 7.21–7.17 (m, 3H), 6.73/12.0 (d, 1H), 6.65/12.4 (d, 1H); $\delta^{13}C\{^1H\}$ (ppm): 137.03, 134.67, 133.26, 132.36, 130.41, 129.98, 128.78, 128.04, 127.80, 127.55, 127.41, 126.30, 127.03, 126.75, 125.81, 125.69 {lit. Brooks et al., *J. Am. Chem. Soc.* 121, 5444 (1999): liquid state NMR (CDCl$_3$): $\delta^1H$ (ppm): 7.79–7.74 (m, 1H), 7.73 (s, 1H), 7.64/8.5 (d, 1H), 7.45-7.38 (m, 2H), 7.35/8.8, 1.6 (dd, 1H) 7.30-7.25(m, 2H), 7.24-7.18 (m, 3H), 6.76/12.0 (d, 1H), 6.68/12.4 (d, 1H); $\delta^{13}C\{H_1\}/J_{C-P}$(ppm/Hz): 137.43, 135.07, 133.65, 132.75, 130.80, 130.38, 129.18, 128.43, 128.19, 128.15, 127.81, 127.68, 127.42, 127.14, 126.20, 126.08}.

Example 11

This example illustrates the preparation of 2-ethenylnaphthalene (IXb), FIG. 5.

2-ethenylnaphthalene (IXb) was prepared from 0.90 g (2.52 mmol) of (methyl)triphenylphosphonium bromide (Vb), 0.33 g (2.56 mmol) of naphthaldehyde and 1.06 g (7.68 mmol) of anhydrous K$_2$CO$_3$ by ball-milling for a total of 20 hours. The mechanical processing was interrupted after five, ten and 16 hours and the samples for analysis where extracted from the vial in a glove box under helium, then the vial was resealed and ball-milling continued. After 20 hours of mechanical treatment, the formed powder was analyzed by the solid- and liquid state NMR spectroscopy, then 1.76 g of the powder was loaded on the top of a silica gel chromatography column, and the compound IXb was isolated by eluation with a hexane—toluene mixture in the 73% yield, (0.21 g). Triphenylphosphine oxide was further obtained from the same column in 80% yield (0.39 g) using a hexane-acetone mixture as an eluant. The $^{31}$P NMR spectrum of the powder after ball-milling for 20 h contained two signals: a major signal corresponding to triphenylphosphine oxide at $\delta^{31}$P=25 ppm and a very weak signal from the starting phosphonium salt Vb at $\delta^{31}$P=21 ppm.

2-Ethenylnaphthalene (IXb): Liquid state NMR (CDCl$_3$): $\delta^1$H/J$_{H-H}$ (ppm/Hz): 7.75–7.69 (m, 4H, Ph), 7.58/8.8, 1.2 (dd, 1H, Ph), 7.43–7.37 (m, 2H, Ph) 6.83/17.6, 10.9 (dd, 1H, CH), 5.83/17.6 (d, 1H, CH), 5.29/10.9 (d, 1H, CH); $\delta^{13}$C{$^1$H} (ppm): 136.86, 134.92, 133.49, 133.08, 128.08, 127.98, 127.59, 126.32, 126.14, 125.82, 123.08, 114.08 {lit. (Katritzky, et al., *Magn. Reson. Chem.* 29, 2 (1991)): liquid state NMR (CDCl$_3$): $\delta^1$H/J$_{H-H}$ (ppm/Hz): 7.71, 7.70, 7.65, 7.55, 7.38, 7.36, 6.80/17.6, 10.9 (dd, CH), 5.80/17.6 (d, CH), 5.27/10.9 (d, CH); $\delta^{13}$C{$^1$H} (ppm):136.86, 134.92, 133.49, 133.09, 128.09, 127.99, 127.60, 126.35, 126.15, 125.83, 123.07, 114.07};MS (70 eV, EI): m/z (%): 154 (100) [M$^+$], 128 (11); Mp 58–61° C. {lit.: 61–62° C. (Ando, et al., *J. Organomet. Chem.* 133, 219 (1977))}.

Example 12

This example illustrates the preparation of 1-(4-bromophenyl)-1-methyl-2-phenylethylene (IXc), FIG. 5.

1-(4-Bromophenyl)-1-methyl-2-phenylethylene (IXc) was prepared from 0.85 g (2.18 mmol) of (benzyl)triphenylphosphonium chloride (Vc), 0.44 g (2.20 mmol) of p-bromoacetophenone and 0.5 g (3.62 mmol) of anhydrous K$_2$CO$_3$ by ball-milling for 14 hours. The formed powder was analyzed by the solid state $^{31}$P MAS NMR spectroscopy. The solid state $^{31}$P MAS NMR spectrum of the ball-milled powder contained two signals: a major signal corresponding to triphenylphosphine oxide at $\delta^{31}$P =25 ppm and a minor signal corresponding to the starting phosphonium salt at $\delta^{31}$P=22 ppm, the estimated ratio ~7:1. 1.44 g of the powder was loaded on the top of a silica-gel filled chromatographic column, and the mixture of (E)- and (Z)-isomers was isolated by eluation with a hexane—toluene mixture (E:Z ratio ca. 3.4:1 by $^1$H NMR in CDCl$_3$) in the 70% yield, (0.34 g). Triphenylphosphine oxide was further obtained from the same column in 73% yield (0.36 g) using a hexane-acetone mixture as an eluant. The attempt to separate the (E)- and (Z)-isomers was unsuccessful. Assignment of the signals in the $^1$H NMR spectrum of the reaction products was performed according to the literature (see, e.g., Beller, et al., *Eur. J. Inorg. Chem.* 1998, 29).

1-(4-Bromophenyl)-1-methyl-2-phenylethylene (IXc): Liquid state NMR (CDCl$_3$): $\delta^1$H/J$_{H-H}$ (ppm/Hz): 7.45–7.43 (m, Ph), 7.36–7.32 (m, Ph), 7.25–7.21 (m, Ph) 7.10–7.01 (m, Ph), 6.94–6.92 (m, Ph) 6.79 (s, CH E-isomer), 6.46 (s, CH, Z-isomer), 2.21/1.3 (d, CH$_3$, E-isomer), 2.1/1.4 (Z-isomer); $\delta^{13}$C{$^1$H} (ppm):142.81, 140.92, 138.02, 137.29, 137.26, 136.29, 131.69, 131.45, 130.11, 129.22, 129.20, 129.04, 128.32, 128.25, 128.23, 128.09, 127.71, 127.38, 126.79, 126.44, 121.17, 120.92, 29.98, 26.96, 17.57; MS (70 eV, EI): m/z (%): 272/274 (53/57) [M$^+$], 191 (24) [M$^+$-Br], 178 (100),165 (15), 152 (12), 115(65), 102 (22), 89 (30) 77 (29).

Example 13

This example illustrates the preparation of 1-(ethyl)-2-(naphthyl)ethylene (IXd), FIG. 5.

1-(ethyl)-2-(naphthyl)ethylene (IXd) was prepared from 1.00 g (2.7 mmol) of (ethyl)triphenylphosphonium bromide (Vd), 0.42 g (2.7 mmol) of naphthaldehyde and 0.79 g (5.5 mmol) of anhydrous K$_2$CO$_3$ by ball-milling for 26 hours. The formed powder was analyzed by the solid state $^{31}$P MAS NMR spectroscopy. The solid state $^{31}$P MAS NMR spectrum of the ball-milled powder contained two signals: a major signal corresponding to triphenylphosphine oxide at $\delta^{31}$P=25 ppm and a minor signal corresponding to the starting phosphonium salt at $\delta^{31}$P=30 ppm, the estimated ratio ~8:1. The powder (2.0 g) was loaded on the top of a silica-gel filled chromatographic column, and the mixture of (E)- and (Z)-isomers was isolated by eluation with a hexane-toluene mixture (E:Z ratio ca. 1:1 by $^1$H NMR in CDCl$_3$) in the 63% yield, (0.26 g). Triphenylphosphine oxide was further obtained from the same column in 80% yield (0.61 g) using a hexane-acetone mixture as an eluant. Assignment of the signals in the $^{13}$C and $^1$H NMR spectra of the reaction products was performed according to the literature (see, e.g., Kulasegarm, et al., *J. Org. Chem.* 62, 6547 (1997); Kulasegarm et al., *Tetrahedron* 54, 1361(1998)).

1-(ethyl)-2-(naphthyl)ethylene (IXd): Liquid state NMR (CDCl$_3$): $\delta^1$/J$_{H-H}$(ppm/Hz): 7.83–7.45 (m, Ph), 7.66 (s, Ph), 7.58–7.55 (m, Ph), 7.48–7.40, 6.63–6.54 (m, CH E- and Z-isomer), 6.40–6.31 (m, CH, E-isomer), 5.90–5.86 (m, E-isomer), 2.01/7.3, 1.4 (dd), 1.94/6.4, 1.3 (dd) (CH$_3$, E- and Z-isomer); $\delta^{13}$C{I$^1$H} (ppm): 135.53, 135.30, 133.89, 133.53, 132.79, 132.29, 131.34, 130.08, 128.20, 128.08, 128.07, 127.99, 127.77, 127.74, 127.73, 127.66, 127.47, 127.36, 126.24, 125.15, 125.78, 125.55, 125.37, 123.66, 18.8, 14.97 MS (70 eV, EI): m/z (%): 168 (100) [M$^+$], 153 (28) [M$^+$-CH$_3$], 141 (10), 115(9)

Example 14

This example illustrates the preparation of 4-bromostyrene (IXe), FIG. 5.

4-bromostyrene (IXe) was prepared from 1.15 g (3.22 mmol) of (methyl)triphenylphosphonium bromide (Vb), 0.60 g (3.24 mmol) of p-bromoacetophenone and 1.50 g (10.8 mmol) of anhydrous K$_2$CO$_3$ by ball-milling for 22.5 hours. The formed powder was analyzed by the solid state $^{31}$P MAS NMR spectroscopy. The solid state $^{31}$P MAS NMR spectrum of the ball-milled powder contained the signal at $\delta^{31}$P=25 ppm corresponding to triphenylphosphine oxide. The powder (2.5 g) was used for the separation of 4-bromostyrene (IXe) by distillation in vacuum. B. p. 38° C. at 0.1 mm of Hg. The yield 60% (0.34 g). Assignment of the signals in the $^{13}$C and $^1$H NMR spectra of Xe was performed according to the literature (see, e.g., Happer et al., *J. Chem. Soc. Perkin Trans. II* 1984, 1673; Echavarren et al., *J. Am. Chem. Soc.* 109,5485 (1987)).

4-bromostyrene (IXe): Liquid state NMR (CDCl$_3$): $\delta^1$H/J$_{H-H}$ (ppm/Hz): 7.43–7.41 (m, Ph), 7.24–7.23 (m, Ph), 6.62/17.4, 10.9 (dd, CH), 5.72/17.5 (d, CH$_2$), 5.25/10.9 (d, CH$_2$); $\delta^{13}$C{$^1$H} (ppm):136.28, 135.55, 131.45, 127.60, 121.45, 114.45

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preparing a phosphonium salt of the formula [$R^1R^2R^3P$—$CR^4R^5R^6$]X, which method comprises ball-milling a phosphine of the formula $R^1R^2R^3P$ with a compound of the formula $XCR^4R^5R^6$;

wherein $R^{1-3}$ are independently selected from the group consisting of hydrogen, $C_{1-25}$ alkyl, $C_{3-8}$ cycloalkyl, aralkyl, and aryl;

wherein $R^{4-6}$ are independently selected from the group consisting of hydrogen, $C_{1-25}$ alkyl, $C_{3-8}$ cycloalkyl, aralkyl, and aryl;

wherein X is a mono- or polyvalent anion; and wherein the method optionally takes place in one reaction vessel.

2. The method of claim 1, wherein the phosphonium salt is selected from the group consisting of propane-1,3-diyl-bis(triphenylphosphonium) dibromide—, and (2-naphthalenylmethyl)triphenylphosphonium bromide.

3. A method of preparing a phosphorus ylide of the formula $R^1R^2R^3P$=$CR^4R^5$, which method comprises ball-milling a phosphonium salt of the formula [$R^1R^2R^3P$—$HCR^4R^5$]X in the presence of a base;

wherein $R^{1-3}$ are independently selected from the group consisting of hydrogen, $C_{1-25}$ alkyl, $C_{3-8}$ cycloalkyl, aralkyl, and aryl;

wherein $R^4$ and $R^5$ are independently selected from the group consisting of hydrogen, $C_{1-25}$ alkyl, $C_{3-8}$ cycloalkyl, aralkyl, and aryl;

wherein X is a mono- or polyvalent anion; and wherein the method optionally takes place in one reaction vessel.

4. The method of claim 3, wherein the base is $K_2CO_3$.

5. The method of claim 3, wherein the phosphonium salt of the formula [$R^1R^2R^3P$—$HCR^4R^5$]X, is formed using a method comprising ball-milling a phosphine of the formula $R^1R^2R^3P$ with a compound of the formula $HCR^4R^5X$;

wherein $R^{1-3}$ are independently selected from the group consisting of hydrogen, $C_{1-25}$ alkyl, $C_{3-8}$ cycloalkyl, aralkyl, and aryl;

wherein $R^4$ and $R^5$ are independently selected from the group consisting of hydrogen, $C_{1-25}$ alkyl, $C_{3-8}$ cycloalkyl, aralkyl, and aryl; and wherein X is a mono- or polyvalent anion.

6. A method of preparing a phosphonium salt selected from the group consisting of phenacyltriphenylphosphonium bromide and (α-benzoyl-α-phenylmethylene)-triphenylphosphonium bromide, which method comprises ball-milling triphenylphosphine with phenacyl bromide or α-benzoyl-α-phenylmethylene bromide to produce the corresponding phosphonium salt; and wherein the method optionally takes place in one reaction vessel.

7. The method of claim 6, wherein the phosphonium salt is phenacyltriphenylphosphonium bromide.

8. The method of claim 6, wherein the phosphonium salt is (α-benzoyl-α-phenylmethylene)-triphenylphosphonium bromide.

9. A method of preparing a phosphorus ylide selected from the group consisting of benzoylmethylenetriphenylphosphorane, (α-benzoyl-α-phenylmethylene)triphenylphosphorane, and (carbethoxymethylene)-triphenylphosphorane, which method comprises ball-milling a corresponding phosphonium salt in the presence of a base; and wherein the method optionally takes place in one reaction vessel.

10. The method of claim 9, wherein the phosphorus ylide is benzoylmethylenetriphenylphosphorane.

11. The method of claim 9, wherein the phosphorus ylide is (α-benzoyl-α-phenylmethylene)triphenylphosphorane.

12. The method of claim 9, wherein the phosphorus ylide is (carbethoxymethylene)-triphenylphosphorane.

* * * * *